United States Patent [19]

Chalk et al.

[11] Patent Number: 4,515,711

[45] Date of Patent: May 7, 1985

[54] ALKENOXY OCTADIENES AS ODORANTS

[75] Inventors: Alan J. Chalk, Kinnelon; Kenneth L. Purzycki, Lake Parsippany, both of N.J.

[73] Assignee: Givaudan Corporation, Clifton, N.J.

[21] Appl. No.: 423,901

[22] Filed: Sep. 27, 1982

[51] Int. Cl.$^3$ ............................................... A61K 7/46
[52] U.S. Cl. ................................................ 252/522 R
[58] Field of Search .................................... 252/522 R

[56] References Cited

U.S. PATENT DOCUMENTS 3,499,042  3/1970  Smutny ................................ 568/690
3,840,605  12/1974  Gordon ............................ 260/614 R

FOREIGN PATENT DOCUMENTS 1807491  6/1969  Fed. Rep. of Germany .
2154370  5/1973  Fed. Rep. of Germany .
1174404  12/1969  United Kingdom .
1256357  12/1971  United Kingdom .

OTHER PUBLICATIONS

McAdoo et al., "C.A.", vol. 81, (1974), 161112a.
Kropp et al., "J. Am. Chem. Soc.", vol. 98, No. 25, (12/1976), pp. 8135–8144.
Davidson, et al., "J. Organic Chemistry", vol. 47, No. 10, (5/1982), pp. 1904–1909.
Biellmann et al., "Tetrahedron Letters", No. 43, (1979), pp. 4209–4210.
McKillop et al., "Tetrahedron Letters", vol. 30, (1974), pp. 2467–2475.
V. J. Beger and H. Reichel, J. Prakt. Chem. 315, 1067–1076, (1973).
Y. Tamaru et al., Chem. Lett. 1329–1332, (1978).
R. L. Augustine, *Catalytic Hydrogenations*, 1965, Marcel Dekker Inc., N.Y., Chap. 4, pp. 57–60.

*Primary Examiner*—Anton H. Sutto
*Attorney, Agent, or Firm*—Robert F. Tavares

[57] ABSTRACT

Alkenoxy octadienes and alkoxy octadienes and octanes are valuable fragrance materials.

4 Claims, No Drawings

ALKENOXY OCTADIENES AS ODORANTS

SUMMARY OF THE INVENTION

The present invention is concerned with fragrance compositions, and methods for preparing same, which contain an olfactorily effective amount of an ether of the formula

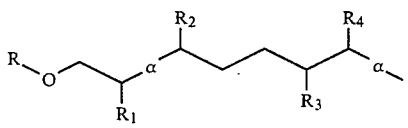

wherein:
  α represents a single or double carbon-carbon bond;
  R is an alkyl or alkenyl group of one to four carbon atoms such that when α is a single carbon-carbon bond R is alkyl; and
  $R_1$, $R_2$, $R_3$ and $R_4$ are all hydrogen or two of them are methyl groups provided that $R_1$ and $R_2$ are not both methyl and $R_3$ and $R_4$ are not both methyl and isomeric mixtures thereof. The compounds of formula I are alkoxy or alkenoxy octadienes when α is a double bond and alkoxy octanes when α is single bond.

The ethers of formula I possess a common odor character that can be classified as fruity in nature and which can be effectively used in the development of novel fragrance formulations, especially formulations developed for use in functional products as soaps, cosmetics, detergents, cleaning products and the like. Those ethers in which all the carbon-carbon bonds are single bonds are particularly valuable for use in strongly oxidizing cleaning products such as a bleach.

A number of methods are known in the art for preparing alkadienyl ethers by reacting a diene such as isoprene or butadiene in the presence of an alcohol and a suitable catalyst. [See for example U.S. Pat. No. 3,499,042; British Pat. No. 1,256,357; German Pat. No. 1,807,491; J. Prakt. Chem. 315 1067 (1973); Chem. Lett. 1329 (1978)]. When butadiene is reacted in the presence of an alkyl or alkenyl alcohol and a suitable catalyst, there is formed a 2,7-octadienyl alkyl or alkenyl ether. When isoprene is used in place of butadiene, there is the possibility for isomeric mixtures depending on whether the isoprene units add head to tail, tail to tail or head to head. The predominant isomer is the 2,6-dimethyl-2,7-octadienyl alkyl or alkenyl ether resulting from a head to tail dimerization and this isomer accounts for about 75%±5% of the isomeric mixture. The minor isomers result from tail to tail dimerization (3,6-dimethyl-2,7-octadienyl alkyl or alkenyl ether) or a head to head dimerization (2,7-dimethyl-2,7-octadiene), the former isomer being present in about 18%±5% and the latter isomer being present in about 8%±5%.

The saturated ethers may be prepared from the appropriate unsaturated ethers by methods similar to those known in the art for reducing olefinic bonds (See, for example, Robert L. Augustine, *Catalytic Hydrogenations*, 1965, Marcel Dekker, Inc. N.Y. Chap. 4 pp 57–60).

Many of the unsaturated ethers have been reported in the prior art, but no odor properties nor utility as a fragrance material has been reported. The saturated ethers are novel compounds.

DESCRIPTION OF THE PREFERRED EMBODIMENTS

Although each of the ethers of formula I can be described as having a clean and pleasant fruity odor character, each differs one from the other in the nature of this character. For example, in one compound the fruity odor may be more reminiscent of pineapple while in another it may be more reminiscent of orange or melon. Other odor notes, such as green, floral and fatty may also be present in varying degrees of strength and character and the blending of these notes with the aforementioned individual fruity notes provides each of the ethers of formula I with its own individual odor character.

The predominant odor characteristics appear to be affected by the degree of unsaturation in the octyl group. For example, a specific type of fruity odor, namely fatty-citrusy, appears to stand out in the case of the saturated alkoxy octanes while in the case of the unsaturated alkoxy and alkenoxy octadienes, a green odor appears to dominate along with the fruity odor.

The clean pleasant nature of their odors makes these ethers particularly suitable for adding a distinctive quality to fragrance formulations; that is a green and fruity or citrusy character. They are also useful for providing nuances to formulations such as adding lift to topnotes or enhancement of the basic odor impression.

Those ethers which have a predominantly fatty-citrusy odor character are useful in combination with other odorants in the creation of fragrance formulations of the citrus type such as lemon, lime and the like, where they contribute to the basic odor impression of the fragrance. They are particularly suitable for the preparation of fragrances that are described as "fresh" and "clean".

Those ethers which have a more predominantly green and fruity odor character can be effectively used in the creation of fragrance formulations of the herbaceous, camphoraceous, piney, floral, chypré and cologne-blend especially floral bases. Of these ethers, 1-(2-propenoxy)-2,7-octadiene possesses the best aesthetic balance of green and fruity odor notes and is especially preferred for such applications. The greenness of its character is the most pleasing and longest lasting. It may be suitably used in formulations to provide a distinguishing odor character to the base, or in low concentrations, e.g. about 0.2%, for providing special nuances.

The 1-(2-propenoxy)-2,7-octadiene is especially useful in improving floral bases such as green florals and fruity-green florals. A green floral formulation without the compound was perceived to be incomplete with the green notes present tending to stand out individually from the composition. Similarly in a fruity-green floral base without the compound the fruity character was found to be somewhat flat and undeveloped. The addition of 1-(2-propenoxy)-2,7-octadiene to these bases blended the individual green notes in the green floral enhancing its basic character and developed the fruity character in the fruity-green floral. Both bases also benefited by the fact that the topnote appeared more diffusive giving greater lift to the fragrances. The overall impression was that of finished, balanced compositions.

In a specific floral composition in the direction of hyacinthe, the addition of 1-(2-propenoxy)-2,7-octadiene imparted the stemy-green note that is found naturally in the hyacinthe flower. The overall green character of the fragrance was enhanced resulting in a fuller, rounder floral impression.

The 1-(2-propenoxy)-2,7-octadiene was used advantageously at low concentrations in providing nuances to formulations. At 0.2% in a cologne base, in the direction of citrus, it enhanced the neroli, citrus character of the base imparting greater intensity and freshness.

The fragrance compositions to which the ethers of the invention may be suitably added, can be used as odorant bases for the preparation of perfumes, toilette waters and the like. Because of the overall nature of their odor character these ethers are particularly suitable for the preparation of odorant bases to be used in the preparation of functional products including but not limited to, hand creams, cold creams, lotions, deodorants, dipilatory creams, shampoos, soaps, detergents, room sprays and the like. The alkoxy octanes of formula I are particularly suitable for masking, modifying or enhancing the odor of cleaning products such as a bleach product. They have been tested and found to be stable in 5–6% aqueous sodium hypochlorite solutions. Neither the oxidizing power of the solution nor the olfactive integrity of the odorant was deliteriously affected even after standing several weeks at room temperature.

The ethers of formula I may be used in the production of fragrance compositions in the practical range of from about 0.1% to 15%. This range however, is not to be considered as being limiting, as special effects may be achieved at much higher percentages, the amount used being limited only by the effect desired and the imagination of the perfumer.

Fragrance compositions containing compounds of formula I may be added in the usual manner to perfumed goods in practical limits from about 0.1% in the case of detergents to about 30% in the case of alcoholic solutions. For those fragrance compositions to be used in cleaning products, as bleach, a practical range of about 0.1% to 0.25% is preferred. These ranges, however, should not be considered as limiting as higher or lower percentages may be used depending on the preferences of the perfumer.

The following examples illustrate the present invention as it is now preferred to practice it and are not to be construed as limiting.

EXAMPLE I

This example illustrates preparation of compounds of formula I.

A. Alkoxy and Alkenoxy Octadienes

General Procedures:
1. Approximately 2.8 moles of the appropriate diene and 2 moles of the appropriate alcohol were reacted at 80°–90° in a pressure bottle in the presence of palladium acetate (0.096 g), triphenylphosphine (0.11 g) and a 40% solution of Triton B in the reactant alcohol (20 ml) at autogeneous pressure for up to 18 hrs.
2. Approximately 2 moles of butadiene and 1.5 moles of the appropriate alcohol were reacted in a pressure bottle at 100° in the presence of palladium chloride (0.088 g) sodium p-toluene sulfinate (0.44 g) water (4 ml) and a 40% solution of Triton B in the reactant alcohol (20 ml) at autogeneous pressure for 1 week.

The octadienes prepared by procedure 1 and their odor descriptions are:

1-(2-Propenoxy)-2,7-octadiene; b.p. 91°–92° C. @ 10 mm Hg; odor: pineapple, green. opopanax, lavender.

1-(2-Methyl-2-propenoxy)-2,7-octadiene; b.p. 95° C. @ 8 mm Hg; odor: pineapple, bergamot, fruity, citrus.

2,6-(3,6- and 2,7-) Dimethyl-1-methoxy-2,7-octadiene (75% of 2,6-isomer); b.p. 55°–58° C. @ 2 mm Hg; odor: fruity, citrus, rosy, green.

2,6-(3,6- and 2,7-) Dimethyl-1-(2-propenoxy)-2,7-octadiene (75% of 2,6-isomer); b.p. 87°–94° C. @ 4 mm Hg; odor: pineapple, fruity, citrus, bready.

The octadienes prepared by procedure 2 and their odor descriptions are:

1-Methoxy-2,7-octadiene; b.p. 111° C. @ 100 mm Hg; odor: green, fatty, violet, fruity.

1-(2-Methylpropoxy)-2,7-octadiene; b.p. 93° C. @ 10 mm Hg; odor: green, fatty, leafy, fruity, pineapple.

1-(3-Buten-2-oxy)-2,7-octadiene; b.p. 90° C. @ 10 mm Hg; odor: fruity, leafy, green, Estragole.

B. Alkoxy octanes

The appropriate alkoxy or alkenoxy octadiene as prepared in A, was reduced over palladium on carbon and was used without further purification. The alkoxy octanes prepared by this procedure, and their odor descriptions are:

1-Propoxyoctane; fatty, citrus.

1-(2-Methylpropoxy)-octane; fresh, citrus, fruity, fatty. 2,6-(3,6- and 2,7-)Dimethyl-1-methoxyoctane (75% of 2,6-isomer); fresh, citrus, melon.

2,6-(3,6- and 2,7-)Dimethyl-1-propoxyoctane (75% of 2,6-isomer); melon, orange.

EXAMPLE II

This example illustrates the use of 1-(2-Propenoxy)-2,7-octadiene in fragrance compositions. The components are given in parts per thousand by weight.

| A. Green - Floral Base Components | Parts |
| --- | --- |
| Benzyl Acetate | 65 |
| Benzyl Isobutyrate | 10 |
| Cyclamen Aldehyde | 25 |
| Citronellol | 40 |
| Dimetol ® (2,6-dimethylheptan-2-ol) | 15 |
| Ethyl Linalool | 65 |
| Galbanum Oil | 5 |
| Gardenol ® (α-Methylbenzyl Acetate) | 7 |
| Geranyl Acetone | 120 |
| Ylang Oil | 20 |
| Hexyl Cinnamic Aldehyde | 80 |
| Isobutyl Acetate | 7 |
| Isobutyl Linalool | 40 |
| Isocyclocitral | 5 |
| Lilial ® (p-tert-Butyl-α-methylhydrocinnamaldehyde) | 30 |
| Linalool Synthetic | 40 |
| Linalyl Benzoate | 30 |
| Laurine ® (Hydroxycitronellal) | 50 |
| Neral | 25 |
| Nerolidol | 60 |
| Phenyl Ethyl Isobutyrate | 13 |
| Phenyl Ethyl Alcohol | 25 |
| Tetrahydrolinalool | 50 |
| Dipropylene Glycol | 153 |
| | 980 |

The fragrance of the above green-floral base was found to be unfinished; the green notes were perceived to stand out individually creating an inbalance in the blend. The addition of 2% (20 parts) of 1-(2-propenoxy)-2,7-octadiene blended the individual green notes into the base and enhanced the overall green character. Additionally, it imparted roundness and greater lift to the fragrance resulting in a finished, balanced composition.

| B. Fruity - Green Floral Base Components | Parts |
|---|---|
| Crysolide ® (4-Acetyl-6-tert-butyl-1,1 dimethylindan) | 20 |
| Aldehyde C-14 | 30 |
| Aldehyde C-16 (10% in dipropylene glycol) | 2 |
| Isoamylphenylethyl Ether | 20 |
| Allyl-α-ionone | 50 |
| Citronellal pure | 1 |
| Dimethylbenzylcarbinyl Acetate | 30 |
| Dipropylene Glycol | 462 |
| Gardenol ® (α-Methylbenzyl Acetate) | 50 |
| Lavandin Oil | 200 |
| Lilial ® (p-tert-Butyl-α-methylhydrocinnamaldehyde) | 5 |
| 2,4-Dimethyl-3-cyclohexene-1-carboxaldehyde | 5 |
| Verdyl Acetate | 100 |
| | 975 |

The above floral base was found to be somewhat flat and lacking a developed fruity character. The addition of 2.5% (25 parts) of 1-(2-propenoxy)-2,7-octadiene enhanced the fruity notes of the composition adding more diffusion to the topnotes resulting in a finished composition.

| C. Hyacinthe Fragrance Components | Parts |
|---|---|
| Benzyl Acetate | 80 |
| Phenyl Ethyl Alcohol | 260 |
| Cinnamic Alcohol Substitute | 100 |
| Benzyl Acetate | 50 |
| Hexyl Cinnamic Aldehyde | 20 |
| Indole Pure | 1 |
| Phenyl Acetaldehyde pure (50% in Dipropylene Glycol) | 10 |
| Heliotropin Recryst. | 20 |
| Fixolide ® Prime (7-Acetyl-1,1,3,4,4,6-hexamethyltetralin) | 20 |
| Lilial ® (p-tert-Butyl-α-methylhydrocinnamaldehyde) | 50 |
| Clove Leaf Redist. | 10 |
| Amyl Salicylate | 100 |
| Terpineol Extra | 40 |
| Amyl Cinnamic Aldehyde | 45 |
| Galbanum Sol. Resin | 10 |
| Benzyl Cinnamate | 50 |
| Phenyl Ethyl Dimethyl Carbinol | 30 |
| Hexenyl Salicylate | 10 |
| Dipropylene Glycol | 54 |

| C. Hyacinthe Fragrance Components | Parts |
|---|---|
| *-continued* | |
| | 960 |

The hyacinthe fragrance was found to be somewhat flat and lacking the fullness of a natural hyacinthe. The addition of 4% (40 parts) of 1-(2-propenoxy)-2,7-octadiene added a stemy-green note that is found naturally in a hyacinthe flower and enhanced the green character of the fragrance resulting in a fuller, rounder floral.

| D. Cologne Base Components | Parts |
|---|---|
| Musk Ketone | 10 |
| Fixolide ® Prime (7-Acetyl-1,1,3,4,4,6-hexamethyltetralin) | 15 |
| Estragole | 5 |
| Bergamot Oil | 180 |
| Dimetol ® (2,6-Dimethylheptan-2-ol) | 5 |
| Helional ™ (IFF) (2-Methyl-3,4-methylenedioxyhydrocinnamaldehyde) | 20 |
| Lemon Oil NS | 130 |
| Lilial ® (p-tert-Butyl-α-methylhydrocinnamaldehyde) | 20 |
| Linalyl Acetate Synth. | 200 |
| Neroli 27/NSC (Givaudan Specialty Base) | 10 |
| Petitgrain Retif. | 40 |
| Rosemary Oil | 40 |
| Terpinyl Acetate | 50 |
| Lavandin Pure | 10 |
| Phenyl Ethyl Alcohol Prime | 10 |
| Sage Clary Natural | 5 |
| Hexyl Cinnamic Aldehyde | 80 |
| Benzyl Acetate | 10 |
| Oranger Crystal | 5 |
| Benzyl Salicylate | 40 |
| Foin Absolute | 1 |
| Vetiver Acetate B Extra | 20 |
| Anethol USP | 3 |
| Bay Oil | 3 |
| Dipropylene Glycol | 86 |
| | 998 |

The above Cologne base, in the direction of citrus, was lacking in roundness and intensity. The addition of 0.2% (2 parts) of 1-(2-Propenoxy)-2,7-octadiene enhanced the citrus, neroli character resulting in an increase in intensity and freshness.

We claim:

1. A fragrance composition comprising an olfactorily effective amount of the compound 1-(2-propenoxy)-2,7-octadiene and at least one other olfactory substance.

2. A composition according to claim 1 in which the fragrance composition is of the floral type.

3. A method for improving the odor of a fragrance composition by adding thereto an olfactorily effective amount of the compound 1-(2-propenoxy)-2,7-octadiene.

4. The method according to claim 3 wherein the fragrance composition to be improved is of the floral type.

* * * * *